United States Patent [19]

Aoki et al.

[11] 4,166,129
[45] Aug. 28, 1979

[54] AGRICULTURAL AND HORTICULTURAL N-BENZOYL-N'-TRICHLOROETHYLIDENE HYDRAZINE FUNGICIDES

[75] Inventors: Katsumichi Aoki; Susumu Shimizu; Keigo Satake; Shiro Yamazaki; Nobuo Hatakeyama, all of Iwaki, Japan

[73] Assignee: Kureha Kagaku Kogyo Kabushiki Kaisha, Tokyo, Japan

[21] Appl. No.: 845,398

[22] Filed: Oct. 25, 1977

[30] Foreign Application Priority Data

Oct. 28, 1976 [JP] Japan .................. 51-128864
Oct. 28, 1976 [JP] Japan .................. 51-128865
Jul. 28, 1977 [JP] Japan .................. 52-090631

[51] Int. Cl.² ............... C07C 109/18; A01N 9/20
[52] U.S. Cl. ............... 424/324; 260/558 H; 260/559 H
[58] Field of Search ............... 424/324; 260/558 H, 260/559 H

[56] References Cited

U.S. PATENT DOCUMENTS

| | | | |
|---|---|---|---|
| 2,767,173 | 10/1956 | Katz | 260/558 H X |
| 3,836,580 | 9/1974 | Bruce | 260/558 H |
| 3,886,211 | 5/1975 | Keenan | 260/558 H X |
| 4,071,633 | 1/1978 | Aoki et al. | 260/558 H X |

FOREIGN PATENT DOCUMENTS 659441 3/1963 Canada ..................... 260/558 H
1022218 1/1958 Fed. Rep. of Germany ...... 260/558 H

OTHER PUBLICATIONS

Offe et al., CA 47:3929(a), 1953.
Kametani et al., CA 62:16110g (1965).
Stroh et al., CA 67:73299x (1967).
Aoki et al., CA 85:187782b (1976).

*Primary Examiner*—Thomas Waltz
*Attorney, Agent, or Firm*—Fleit & Jacobson

[57] ABSTRACT

This invention provides novel fungicidal compositions comprising a carrier and a fungicidally effective amount of a compound having the general formula

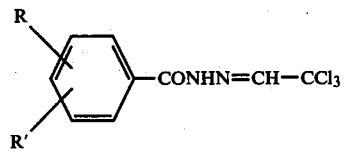

wherein each of R and R' stands for a member of the group consisting of H, halogen, $CH_3$, $OCH_3$, OH and $NO_2$.

These novel compositions have been found to have a superior fungicidal effect on various plant diseases in the field of agriculture and horticulture.

22 Claims, No Drawings

AGRICULTURAL AND HORTICULTURAL N-BENZOYL-N'-TRICHLOROETHYLIDENE HYDRAZINE FUNGICIDES

BACKGROUND OF THE INVENTION

This invention relates to novel compounds of N-substituted or non-substituted benzoyl-N'-trichloroethylidene hydrazine which may be expressed by the following general formula:

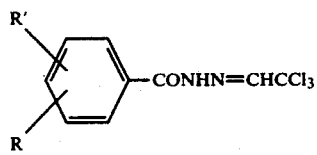

wherein R or R' stands for H, halogen atom, $CH_3$, OH, $OCH_3$ or $NO_2$.

It further relates to novel agricultural and horticultural fungicides having, as their effective substance, at least one of the said chemical compounds.

Various and numerous compounds are hitherto known which are originated from substituted benzoyl hydrazine. Certain reaction products of substituted benzoyl hydrazine with chloral are also known. As an example, N-benzoyl-N'-trichloroethylidene hydrazine is already described in literature [refer to Journal of Pharmaceutical Society of Japan, 85(3), 181(1965)].

In addition N-2-chlorobenzoyl-N'-trichloroethylidene hydrazine is also known [refer to Chem. Absts. 47, 3929a(1953)]. Further, 4-methyl and 4-nitro-derivatives are also known [refer to Chem. Absts. 67. 73299×(1967)].

However, it should be noted that these descriptions relate exclusively to the reaction steps and do not refer to any fungicidal function of these compounds in agricultural and horticultural purposes.

A careful and profound screening study of these known N-substituted and non-substituted benzoyl-N'-trichloroethylidene hydrazine derivatives and novel derivatives synthesized by our selves for the first time, we have found that those selected and found by ourselves have, indeed, remarkable agricultural and horticultural fungicidal effects.

In the following table, our inventive compounds are listed:

Table 1

| No. | Structural formula | Nomination | m.p., °C. | Yield, % |
|---|---|---|---|---|
| 1 | ⟨phenyl⟩—CONHN=CHCCl₃ | N-benzoyl-N'-(2,2,2-trichloroethylidene)hydrazine | 194–5 (decomposition) | 81 |
| 2 | ⟨phenyl, Cl⟩—CONHN=CHCCl₃ | N-2-chlorobenzoyl-N'-(2,2,2-trichloroethylidene)hydrazine | 183–4 (decomposition) | 67 |
| 3 | CH₃—⟨phenyl⟩—CONHN=CHCCl₃ | N-4-methylbenzoyl-N'-(2,2,2-trichloroethylidene)hydrazine | 172–3 (decomposition) | 48 |
| 4 | NO₂—⟨phenyl⟩—CONHN=CHCCl₃ | N-4-nitrobenzoyl-N'-(2,2,2-trichloroethylidene)hydrazine | 169–71 (decomposition) | 51 |
| 5 | ⟨phenyl, Br⟩—CONHN=CHCCl₃ | N-2-bromobenzoyl-N'-(2,2,2-trichloroethylidene)hydrazine | 186–8 (decomposition) | 82 |
| 6 | ⟨phenyl, Br⟩—CONHN=CHCCl₃ | N-3-bromobenzoyl-N'-(2,2,2-trichloroethylidene)hydrazine | 158–9 (decomposition) | 55 |
| 7 | Br—⟨phenyl⟩—CONHN=CHCCl₃ | N-4-bromobenzoyl-N'-(2,2,2-trichloroethylidene)hydrazine | 184–5 (decomposition) | 14 |

Table 1-continued

| No. | Structural formula | Nomination | m.p., °C. | Yield, % |
|---|---|---|---|---|
| 8 | 3-Cl-C6H4-CONHN=CHCCl3 | N-3-chlorobenzoyl-N'-(2,2,2-trichloroethylidene)hydrazine | 149–50 (decomposition) | 60 |
| 9 | 4-Cl-C6H4-CONHN=CHCCl3 | N-4-chlorobenzoyl-N'-(2,2,2-trichloroethylidene)hydrazine | 157–9 (decomposition) | 43 |
| 10 | 2-F-C6H4-CONHN=CHCCl3 | N-2-fluorobenzoyl-N'-(2,2,2-trichloroethylidene)hydrazine | 185–6 (decomposition) | 36 |
| 11 | 3-F-C6H4-CONHN=CHCCl3 | N-3-fluorobenzoyl-N'-(2,2,2-trichloroethylidene)hydrazine | 179–80 (decomposition) | 82 |
| 12 | 4-F-C6H4-CONHN=CHCCl3 | N-4-fluorobenzoyl-N'-(2,2,2-trichloroethylidene)hydrazine | 164–5 (decomposition) | 78 |
| 13 | 2-OH-C6H4-CONHN=CHCCl3 | N-2-hydroxybenzoyl-N'-(2,2,2-trichloroethylidene)hydrazine | 184–5 (decomposition) | 89 |
| 14 | 4-HO-C6H4-CONHN=CHCCl3 | N-4-hydroxybenzoyl-N'-(2,2,2-trichloroethylidene)hydrazine | 221–3 (decomposition) | 85 |
| 15 | 2-I-C6H4-CONHN=CHCCl3 | N-2-iodobenzoyl-N'-(2,2,2-trichloroethylidene)hydrazine | 203–4 (decomposition) | 82 |
| 16 | 3-I-C6H4-CONHN—CHCCl3 | N-3-iodobenzoyl-N'-(2,2,2-trichloroethylidene)hydrazine | 162–3 (decomposition) | 37 |
| 17 | 4-I-C6H4-CONHN=CHCCl3 | N-4-iodobenzoyl-N'-(2,2,2-trichloroethylidene)hydrazine | 183–4 (decomposition) | 20 |
| 18 | 2-OCH3-C6H4-CONHN=CHCCl3 | N-2-methoxybenzoyl-N'-(2,2,2-trichloroethylidene)hydrazine | 122–3 | 60 |
| 19 | 4-CH3O-C6H4-CONHN=CHCCl3 | N-4-methoxybenzoyl-N'-(2,2,2-trichloroethylidene)hydrazine | 163–4 (decomposition) | 33 |

Table 1-continued

| No. | Structural formula | Nomination | m.p., °C. | Yield, % |
|---|---|---|---|---|
| 20 | ⟨o-CH₃-C₆H₄⟩-CONHN=CHCCl₃ | N-2-methyl-benzoyl-N'-(2,2,2-trichloroethylidene)hydrazine | 191-2 (decomposition) | 40 |
| 21 | ⟨m-CH₃-C₆H₄⟩-CONHN=CHCCl₃ | N-3-methyl-benzoyl-N'-(2,2,2-trichloroethylidene)hydrazine | 160-1 (decomposition) | 39 |
| 22 | ⟨o-NO₂-C₆H₄⟩-CONHN=CHCCl₃ | N-2-nitro-benzoyl-N'-(2,2,2-trichloroethylidene)hydrazine | 167-8 (decomposition) | 77 |
| 23 | ⟨5-Cl-2-OH-C₆H₃⟩-CONHN=CHCCl₃ | N-5-chloro-2-hydroxy-benzoyl-N'-(2,2,2-trichloroethylidene)hydrazine | 184-6 (decomposition) | 73 |
| 24 | ⟨4-NO₂-2-Cl-C₆H₃⟩-CONHN=CHCCl₃ | N-2-chloro-4-nitrobenzoyl-N'-(2,2,2-trichloroethylidene)hydrazine | 170-1 (decomposition) | 83 |
| 25 | ⟨2,4-diCl-C₆H₃⟩-CONHN=CHCCl₃ | N-2,4-dichlorobenzoyl-N'-(2,2,2-trichloroethylidene)hydrazine | 181-2 (decomposition) | 70 |
| 26 | ⟨2,5-diCl-C₆H₃⟩-CONHN=CHCCl₃ | N-2,5-dichlorobenzoyl-N' (2,2,2-trichloroethylidene)hydrazine | 167-8 (decomposition) | 57 |
| 27 | ⟨3,4-diCl-C₆H₃⟩-CONHN=CHCCl₃ | N-3,4-dichlorobenzoyl-N'-(2,2,2-trichloroethylidene)hydrazine | 170-1 (decomposition) | 42 |
| 28 | ⟨3,4-di-OCH₃-C₆H₃⟩-CONHN=CHCCl₃ | N-3,4-dimethoxybenzoyl-N'-(2,2,2-trichloroethylidene)hydrazine | 218-20 (decomposition) | 25 |
| 29 | ⟨3,5-diNO₂-C₆H₃⟩-CONHN=CHCCl₃ | N-3,5-dinitro-benzoyl-N'-(2,2,2-trichloroethylidene)hydrazine | 191-2 (decomposition) | 68 |

Remarks:
Compounds 1-4 are known and Compounds 5-29 are unknown.

For the preparation of the foregoing compounds, the procedure may follow substantially in the following reaction:

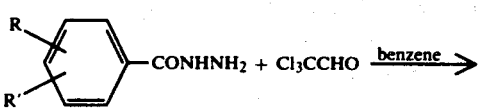

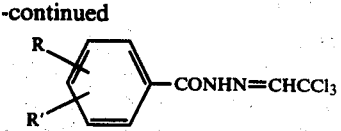

wherein R or R' stands for H, halogen, CH₃, OH, OCH₃ or NO₂;

Or, more specifically, the corresponding acid hydrazide and chloral are refluxed in benzene for 1-3 hours easily to form the desired corresponding product.

In the following, several preferred manufacturing examples will be given for more clear and easy understanding of the invention.

EXAMPLE 1

Preparation of N-benzoyl-N'-(2,2,2-trichloroethylidene)hydrazine (Compound No. 1)

10 g (0.073 mol) of benzoylhydrazine were suspended in benzene, 200 ml, and 18.3 g (0.124 mol) of chloral were added dropwise to the suspension which was then refluxed under agitation for 3 hours. Upon cooling, the sedimented crystals were collected by filtration and washed well with benzene. In this way, white brown crystals, 19 g, were obtained substantially quantatively. m.p. 188°–189° C. (decomposed). When recrystallized from acetone, the Compound No. 1, m.p. 194°–195° (decomposed), was obtained in white needles. Yield: 15.4 g (81% of the theoretical).

SYNTHETIC EXAMPLE 2

Preparation of N-2-bromobenzoyl-N'-(2,2,2-trichloroethylidene)hydrazine (Compound No. 5)

4.2 g (0.02 mol) of 2-bromobenzoyl hydrazine were suspended in benzene, 80 ml, and chloral, 4.7 g (0.032 mol), were added dropwise thereto. The reaction mixture was then refluxed under heating and agitation for 4 hours and under separation of the formed aquous product. Upon cooling, the sedimented white crystals were collected by filtration. These crystals were then recrystallized from a small amount of benzene, thereby to obtain the Compound No. 5 in white crystals. m.p. 186°–188° C., Yield: 5.6 g (82% of the theoretical).

SYNTHETIC EXAMPLE 3

Preparation of N-2-fluorobenzoyl-N'-(2,2,2-trichloroethylidene)hydrazine (Compound No. 10)

2.3 g (0.015 mol) of 2-fluorobenzoyl hydrazine were suspended in benzene, 60 ml, and 3.5 g (0.024 mol) of chloral were added dropwise thereto.

Then the reaction mixture was refluxed under heating and strong agitation for 3.5 hours to separate the formed water therefrom. Upon cooling, the sedimented crystals were collected by filtration and recrystallized from ethanol. In this way, the Compound No. 10 was obtained in weak yellow fine crystals. m.p.: 185°–186° C. (decomposed). Yield: 1.5 g (36% of the theoretical).

SYNTHETIC EXAMPLE 4

Preparaton of N-4-fluorobenzoyl-N'-(2,2,2-trichloroethylidene hydrazine (Compound No. 12)

2.3 g (0.015 mol) of 4-fluorobenzoyl hydrazine were suspended in benzene, 70 ml, and chloral, 3.5 g (0.024 mol) was added dropwise thereto. Then, the reaction mixture was refluxed under heating and strong agitation for 3.5 hours to separate the formed water therefrom. Upon cooling, the sedimented fine crystals were collected by filtration and recrystallized from benzene. In this way, the Compound No. 12 were obtained in fine yellow crystals. m.p.: 164°–165° C. Yield: 3.3 g (78% of the theoretical).

SYNTHETIC EXAMPLE 5

Preparation of N-3-iodobenzoyl-N'-(2,2,2-trichloroethylidene) hydrazine (Compound No. 16)

2.6 g (0.01 mol) of 3-iodo benzoyl hydrazine were suspended in benzene, 100 ml, and chloral, 2.4 g (0.016 mol,) was added dropwise thereto. Then, the reaction mixture was refluxed under heating and strong agitation for 7.0 hours to separate the formed water therefrom.

Upon cooling, a small amount of insoluble constituent was filtered off and the mother liquid was condensed to obtain fine yellow crystals which were then washed with a small amount of benzene. In this way, the Compound No. 16 was obtained in fine white crystals. m.p.: 162°–163° C. Yield: 1.5 g (37% of the theoretical).

SYNTHETIC EXAMPLE 6

Preparation of N-2-methylbenzoyl-N'-(2,2,2-trichloroethylidene)hydrazine (Compound No. 20)

10.2 g (0.068 mol) of 2-methylbenzoylhydrazine were suspended in benzene, 200 ml, a chloral, 16.2 g (0.11 mol) was added dropwise thereto. Then, the reaction mixture was refluxed under heating and strong agitation for 3 hours. Upon cooling, the sedimented fine and white brown crystals were filtered off and washed with benzene.

Then, these crystals were recrystallized from ethanol to obtain the Compound No. 20 in white crystals. m.p.: 191°–192° C. (decomposed). Yield: 8.4 g (45% of the theoretical).

SYNTHETIC EXAMPLE 7

Preparation of N-2-nitrobenzoyl-N'-(2,2,2-trichloroethylidene)hydrazine (Compound No. 22)

1.8 g (0.01 mol) of N-2-nitro benzoyl hydrazine were suspended in benzene, 70 ml, and added with 2.4 g (0.016 mol) of chloral. Then, the reaction mixture was refluxed under heating and strong agitation for 3 hours. Upon cooling, the sedimented white fine crystals were filtered off and washed well with benzene. In this way, the Compound No. 22 was obtained. m.p.: 167°–168° C. (decomposed). Yield: 2.4 g (77% of the theoretical).

SYNTHETIC EXAMPLE 8

Preparation of N-3,4-dichlorobenzoyl-N'-(2,2,2-trichloroethylidene)-hydrazine (Compound No. 27)

4 g (0.02 mol) of N-3,4-dichloro benzoyl hydrazine were suspended in benzene, 80 ml, and added dropwise with chloral, 4.7 g (0.032 mol).

Then, the reaction mixture was refluxed under heating and strong agitation and the residual benzene was distilled off under reduced pressure, to provide weak yellow fine crystals. These crystals were then recrystallized from isopropanol. In this way, the Compound No.

27 was obtained in white fine crystals. m.p.: 170°-171° C. (decomposed). Yield: 2.8 g (42% of the theoretical).

It has been found that the N-substituted benzoyl-N'-trichloroethylidene hydrazine derivatives have a superior fungicidal control power over various and numerous plant disease-inviting fungi, especially those of rice blast; cucumber and grape downy mildew; tomato and potato late blight; cucumber grey mold, wheat leaf rust and the like.

It should be further noted that the inventive derivatives do not include any heavy metal which gives rise to human and animal health problems to which grave social attention was recently directed. On the other hand, these derivatives shown continued and standing control power over various diseases and are generally capable of controlling at least two or more plant diseases derived from the fungous origin. These chemical compounds may be applied per se or in the form of a wettable powder, solution, suspension or the like, as the occasion may require, by mixing with a conventional liquid vehicle or solid or liquid or diluent.

When the inventive derivatives are used as the fungicides or plant disease control agents, any of these derivatives may be mixed with suitable conventional additive(s) acting as spreader(s), developer(s), emulsifier(s), wetting agent(s), adhering or sticking agent(s) and/or the like, in a conventional manner.

Addition of other known medicament(s) is also allowable for further assuring the desired effect and with no fear of deteriolation or decomposition of the effective control agent(s) according to the invention. As an example, such additional medicament may be other known fungicides, insecticide or fertilizers.

In the following, several preferred numerical examples of applicable composition including the effective substance(s) as well as plant disease control effect, are given for clearer understanding of the invention. The parts are given by weight. These parts are shown only by way of example and thus are not limiting.

Composition Example 1

Powdery Composition

|  | Parts |
| --- | --- |
| Compound No. 1 | 3; |
| clay | 40; |
| talc | 57; |

The above constituents are mixed and finely pulverized to provide an applicable powdery blastable composition.

Composition Example 2

Wettable Powdery Composition

|  | Parts |
| --- | --- |
| Compound No. 2 | 50; |
| polyoxyethylene alkylaryl ether | 6; |
| kieselguhr | 44; |

These constituents are mixed together and well pulverized. The resulted powder can be applied with spraying means after being diluted with a proper amount of water.

Plant Test Example 1

Rice Blast Control Test on Planted Pots

Three groups of pots, each group consisting of 30 pots, each pot having a diameter of 10 cm, were used. Japanese rice plants, *Oryza sativa* L, variety: SASANISHIKI, of four leaf stage, were cultured in these pots. Each pot was planted with twenty stems of the rice plant. These plants were well applied with the wettable powder as set forth in the foregoing Composition Example 2, after being diluted with ample amount of water to desired concentration to provide an aqueous suspension. The suspension was applied onto the plants by means of a liquid spray to such degree that all the leaves were well wetted. After drying, the leaves were inoculated with spores of rice blast fungi, *Piricularia oryzae*, by spray of an aqueous suspension thereof. Then, the treated pots were placed in high humidity atmosphere at 27°-28° C. for four days.

Uppermost leaves of the rice plant stems per three pots were precisely reviewed and the observed number of lesions were counted. Equal number of pots having corresponding leaves untreated with the fungicidal suspension were equally inoculated as the control, and the number of lesions was counted, and the control rate was found by the following formula $$\text{Control rate, \%} = \left(1 - \frac{\text{number of lesions on treated leaves}}{\text{number of lesions on untreated leaves}}\right) \times 100$$

The thus determined results are shown in the following Table 2.

Table 2

| Compound No. | Conc., ppm | Test Group 1 *1 | Test Group 1 **2 | Test Group 2 *1 | Test Group 2 **2 | Test Group 3 *1 | Test Group 3 **2 | phytotoxicity |
| --- | --- | --- | --- | --- | --- | --- | --- | --- |
| No. 1 | 500 | 0 | 100 |  |  |  |  | none |
| No. 2 | " | 0 | 100 |  |  |  |  | " |
| No. 3 | " | 0 | 100 |  |  |  |  | " |
| No. 4 | " | 90 | 88.6 |  |  |  |  | " |
| No. 5 | " |  |  |  |  | 0 | 100 | " |
| No. 6 | " |  |  |  |  | 0 | 100 | " |
| No. 7 | " |  |  |  |  | 0 | 100 | " |
| No. 8 | " |  |  | 0 | 100 |  |  | " |
| No. 9 | " |  |  | 79 | 91.0 |  |  | " |
| No. 10 | " |  |  |  |  | 0 | 100 | " |
| No. 11 | " |  |  |  |  | 0 | 100 | " |
| No. 12 | " |  |  |  |  | 0 | 100 | " |
| No. 13 | " |  |  | 0 | 100 |  |  |  |
| No. 15 | " |  |  |  |  | 0 | 100 | " |
| No. 16 | " |  |  |  |  | 0 | 100 | " |
| No. 17 | " |  |  |  |  | 23 | 97.7 | " |
| No. 20 | " |  |  | 0 | 100 |  |  | " |
| No. 21 | " |  |  | 0 | 100 |  |  | " |
| No. 22 | " |  |  | 69 | 92.1 |  |  | " |
| No. 23 | " |  |  | 101 | 88.5 |  |  | " |
| No. 24 | " |  |  | 85 | 90.3 |  |  | " |
| No. 25 | " |  |  | 7 | 99.2 |  |  | " |
| No. 27 | " |  |  | 0 | 100 |  |  | " |
| No. 28 | " |  |  | 135 | 84.6 |  |  | " |
| No. 29 | " |  |  | 175 | 80.1 |  |  | " |
| Non-treated | — | 792 | — | 873 | — | 999 | — | — |

Remarks:
*1 Affected spots number;
**2 Control rate, %

Plant Test Example 2

Pot Test for Control of Downy Mildew on Cucumber Plants

A number of pots of 10 cm diameter, were used for the culture of cucumber plants of two leaf stage, variety: SAGAMI hampaku. Each plant was planted in a pot. Each three pots were grouped into one treating group. These plants were applied with an aqueous suspension of the wettable powder, as set forth in Composition Example 2, after being diluted with water. The application was made by means of a liquid spray. After drying, all the leaves were inoculated with spores of downy mildew fungi, *Pseudoperonospora cubensis*, by spraying. Then, the plants were kept in a high humidity atmosphere at 22°–23° C. for 24 hours, and then in a green house for 5 days. After a lapse of 5 days after said inoculation, the degree of infection was determined by consultation with the following classification, as per one leaf per pot and per three pots for each treating district.

Classification

| Index of Infection | State of Infection |
|---|---|
| "0" | no infection |
| "0.5" | less than 10% infection in terms of inoculated leaf area |
| "1" | 10–20% infection in terms of inoculated leaf area. |
| "2" | 20–40% infection in terms of inoculated leaf area. |
| "3" | 40–60% infection in terms of inoculated leaf area. |
| "4" | 60–80% infection in terms of inoculated leaf area. |
| "5" | over 80% infection in terms of inoculated leaf area. |

The test results are shown in the following Table 3.

Table 3

| Compound No. | Conc.,ppm | Index of Infection, Mean | Phytotoxicity |
|---|---|---|---|
| 1 | 500 | 0 | none |
| 2 | " | 0.5 | " |
| 3 | " | 0 | " |
| 4 | " | 1 | " |
| 5 | " | 0 | " |
| 6 | " | 0.5 | " |
| 7 | " | 0 | " |
| 8 | " | 0 | " |
| 9 | " | 2 | " |
| 10 | " | 0 | " |
| 11 | " | 0.5 | " |
| 12 | " | 0 | " |
| 13 | " | 1 | " |
| 14 | " | 1 | " |
| 15 | " | 2 | " |
| 16 | " | 1 | " |
| 17 | " | 1 | " |
| 19 | " | 0 | " |
| 20 | " | 0 | " |
| 25 | " | 0.5 | " |
| 27 | " | 0 | " |
| 28 | " | 3 | " |
| Non-treated | — | 5 | — |

Plant Test Example 3

Pot Test for the Control of Late Blight on Tomato Plants

A number of pots, each being of 10 cm diameter as before, were planted each with a tomato plant at its four leaf stage, variety being FUKUJU No. 2. Each eight pots were grouped into one treating district. The cultured plants were sprayed with an aqueous suspension of the wettable powder as set forth in the foregoing Composition Example 2. An aqueous suspension of spores of tomato late blight fungi, *Phytophthora infestans*, preparatorily cultured on potato tubers, was sprayed over the above treated tomato leaves after they have been dried. The thus conditioned plants were kept in a green house at 20°–22° C. for two days. After a lapse of four days after the said inoculation, the index of infection was determined in accordance with the foregoing classification, so as to fix the respective mean index of infection per plant. The test results are shown in the following Table 4.

Table 4

| Compound No. | Conc.,ppm | Index of Infection, Mean | Phytotoxicity |
|---|---|---|---|
| 1 | 500 | 0 | None |
| 2 | " | 0.5 | " |
| 3 | " | 0 | " |
| 4 | " | 0.5 | " |
| 5 | " | 0 | " |
| 6 | " | 0.5 | " |
| 7 | " | 0.5 | " |
| 10 | " | 0 | " |
| 11 | " | 0 | " |
| 12 | " | 0 | " |
| 13 | " | 1 | " |
| 15 | " | 1 | " |
| 16 | " | 0 | " |
| 17 | " | 2 | " |
| 18 | " | 2 | " |
| 19 | " | 0 | " |
| 20 | " | 0 | " |
| 22 | " | 2 | " |
| 23 | " | 1 | " |
| 24 | " | 0.5 | " |
| 25 | " | 0.5 | " |
| 26 | " | 1 | " |
| Non-treated | — | 5 | — |

Plant Test Example 4

Pot Test for the Control of Late Blight on Potato Plants

A number of pots, each being of 10 cm diameter as before were planted with potato plants, variety being DANSHAKU, in one-to-one correspondence. Each three pots were grouped into one treating district. These plants were sprayed with an aqueous suspension of the wettable powdery composition as set forth in the Composition Example 2 which was suspended in water to desired concentration.

After drying, an aqueous suspension of spores of potato late blight fungi which had been preparatorily cultured on potato tubers, was sprayed over the planted and pretreated potato leaves for inoculation. Then, the inoculated plants were held in a high humidity atmosphere at 18°–22° C. for two days and then cultured further in a green house. After five days after inoculation, the degree of infection was determined as was classified in the foregoing Plant Test Example 2. The mean degree of infection per pot is shown in each case in the following Table 5.

Table 5

| Compound No. | Conc.,ppm | Index of Infection, Mean | Phytotoxicity |
|---|---|---|---|
| 1 | 500 | 0 | none |
| 2 | " | 0.5 | " |
| 5 | " | 0 | " |
| 7 | " | 0.5 | " |
| 10 | " | 0 | " |
| 11 | " | 0 | " |
| 15 | " | 0.5 | " |
| 17 | " | 1 | " |

Table 5-continued

| Compound No. | Conc.,ppm | Index of Infection, Mean | Phyto-toxicity |
|---|---|---|---|
| 18 | " | 2 | " |
| 21 | " | 0.5 | " |
| 24 | " | 0.5 | " |
| 27 | " | 1 | " |
| 28 | " | 2 | " |
| Non-treated | — | 5 | " |

Plant Test Example 5

Pot Test for the Control of Gray Mold on Cucumber Plants

A number of pots, each being 10 cm diameter as before, were planted with cucumber plants, variety being SAGAMI HAMPAKU, at its two leaf stage in one-to-one correspondence. Each three pots were grouped into one treating district. These plants were sprayed with an aqueous suspension of the wettable powder as set forth in the foregoing Composition Example 2. After drying, cucumber gray mold fungi, *Botrytis cinerea* Persoon, preparatorily cultured on a sugar-added potato-extract-agar culture medium at 20° C. for five days, were fixedly attached to each leaf in the ratio of two circular discs of the fungi-containing agar medium, being of 5 mm diameter, for the execution of inoculation. After inoculation, the treated plants were placed in a green house at 22°–23° C. for five days. The infected leaves were reviewed precisely for the determination of the mean diameter of lesions in mm.

Classification

| Index of Infection | State of Infection |
|---|---|
| "0" | no infection |
| "0.5" | less than 10% infection in terms of inoculated leaf area |
| "1" | 10–20% infection in terms of inoculated leaf area. |
| "2" | 20–40% infection in terms of inoculated leaf area. |
| "3" | 40–60% infection in terms of inoculated leaf area. |
| "4" | 60–80% infection in terms of inoculated leaf area. |
| "5" | over 80% infection in terms of inoculated leaf area. |

The test results are shown in the following Table 6.

Table 6

| Compound No. | Conc.,ppm | Index of Infection, Mean | Phyto-toxicity |
|---|---|---|---|
| 1 | 500 | 0 | none |
| 2 | " | 0 | " |
| 3 | " | 0.5 | " |
| 4 | " | 2 | " |
| 5 | " | 0 | " |
| 6 | " | 0.5 | " |
| 7 | " | 0 | " |
| 8 | " | 0 | " |
| 9 | " | 1 | " |
| 10 | " | 0 | " |
| 11 | " | 0 | " |
| 12 | " | 2 | " |
| 13 | " | 0.5 | " |
| 15 | " | 0 | " |
| 16 | " | 0 | " |
| 17 | " | 2 | " |
| 19 | " | 0.5 | " |
| 20 | " | 0 | " |
| 21 | " | 0 | " |
| 22 | " | 0 | " |
| 25 | " | 0 | " |
| 26 | " | 2 | " |
| 27 | " | 0 | " |

Table 6-continued

| Compound No. | Conc.,ppm | Index of Infection, Mean | Phyto-toxicity |
|---|---|---|---|
| Non-treated | — | 5 | — |

Plant Test Example 6

Pot Test for the Control of Red Rust on Wheat Plants

A number of pots, each being of 10 cm diameter as before, were planted with wheat plants, of three leave stage, variety being NORIN No. 64. Each pot had 16 stems. These plants were sprayed with an aqueous suspension of the wettable composition, as of the foregoing Composition Example 2, of desired concentration, After drying, an aqueous suspension of spores of wheat red rust fungi was sprayed over the pretreated plant leaves, for inoculation and held in a high humidity atmosphere at 20°–25° C. for 24 hours. Then, the pots were preserved in a green house for 7 days. Then, each ten stems were precisely reviewed and the index of infection was measured. Then, the mean value of index of infection per leaf was determined in accordance with the classification set forth in Plant Test Example 2. The results are shown in Table 7.

Table 7

| Compound No. | Conc.,ppm | Index of Infection, Mean | Phyto-toxicity |
|---|---|---|---|
| 1 | 500 | 0 | none |
| 3 | " | 0 | " |
| 5 | " | 0 | " |
| 6 | " | 0.5 | " |
| 8 | " | 0.5 | " |
| 9 | " | 0 | " |
| 12 | " | 0 | " |
| 14 | " | 2 | " |
| 18 | " | 2 | " |
| 19 | " | 0.5 | " |
| 20 | " | 0 | " |
| 23 | " | 1 | " |
| 24 | " | 1 | " |
| 27 | " | 1 | " |
| Non-treated | — | 5 | |

Plant Test Example 7

Pot Test for the Control of Downy Mildew on Grape Plants

A number of pots were planted with grape plant seedlings of two year's culture, variety being NEOMASCUT. These plants were sprayed with an aqueous suspension of the wettable powdery composition as of the foregoing Composition Example 2 to such a degree that all the leaves were well wetted. After drying, these plants were sprayed with an aqueous suspension of pores of grape downy mildew fungi, *Plasmopara viticola* (Barkeley et Curtis) Berlese et de Toni, for inoculation, and held in a high humidity atmosphere at 18°–23° C. Then, the pots were preserved in a green house for 10 days. Each five leaves were reviewed precisely and the mean value of infection index was determined per leaf. The results are shown in Table 8.

Table 8

| Compound No. | Conc.,ppm | Index of Infection, Mean | Phyto-toxicity |
|---|---|---|---|
| 1 | 1,000 | 0 | none |
| 2 | " | 0.5 | " |
| 3 | " | 0 | " |

Table 8-continued

| Compound No. | Conc.,ppm | Index of Infection, Mean | Phytotoxicity |
|---|---|---|---|
| 5 | " | 0 | " |
| 6 | " | 1 | " |
| 9 | " | 0 | " |
| 11 | " | 0.5 | " |
| 12 | " | 0 | " |
| 15 | " | 2 | " |
| 16 | " | 0.5 | " |
| 19 | " | 0 | " |
| 21 | " | 0.5 | " |
| 22 | " | 0 | " |
| 27 | " | 0 | " |
| Non-treated | — | 4 | " |

The embodiments of the invention in which an exclusive property or privilege is claimed are as follows:

1. A fungicidal composition consisting essentially of a carrier and a fungicidally effective amount of a compound having the following general formula:

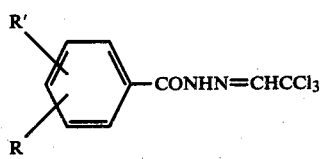

wherein each of R and R' stands for a member of the group consisting of H, halogen, $CH_3$, $OCH_3$, OH and $NO_2$.

2. A method of controlling the growth of fungi on an agricultural plant comprising applying to the plant a fungicidal composition consisting essentially of a carrier and a fungicidally effective amount of a compound of the general formula

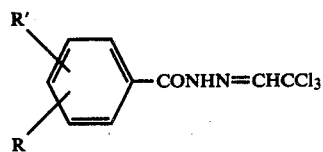

wherein each of R and R' stands for a member of the group consisting of H, halogen, $CH_3$, $OCH_3$, OH and $NO_2$.

3. The method of claim 2 wherein the fungus is rice blast.

4. The method of claim 2 wherein the fungus is cucumber downy mildew.

5. The method of claim 2 wherein the fungus is grape downy mildew.

6. The method of claim 2 wherein the fungus is tomato late blight.

7. The method of claim 2 wherein the fungus is potato late blight.

8. The method of claim 2 wherein the fungus is cucumber gray mold.

9. The method of claim 2 wherein the fungus is wheat leaf rust.

10. The fungicidal composition of claim 2 comprising said compound incorporated in a carrier.

11. The composition of claim 1 wherein R and R' are hydrogen.

12. The composition of claim 1 wherein R is hydrogen and R' is selected from the group consisting of fluoride, chloride, bromide and iodide.

13. The composition of claim 1 wherein R is hydrogen and R' is $CH_3$.

14. The composition of claim 1 wherein R is hydrogen and R' is $NO_2$.

15. The composition of claim 1 wherein R is hydrogen and R' is OH.

16. The composition of claim 1 wherein R is hydrogen and R' is $OCH_3$.

17. The composition of claim 1 wherein R and R' are chloride.

18. The composition of claim 1 wherein the compound is N-5-chloro-2-hydroxy-benzoyl-N'-(2,2,2-trichloroethylidene) hydrazine.

19. The composition of claim 1 wherein the compound is N-2-chloro-4-nitro-benzoyl-N'-(2,2,2-trichloroethylidene) hydrazine.

20. The composition of claim 1 wherein the compound is N-3.4-dichlorobenzoyl-N'-(2,2,2-trichloroethylidene) hydrazine.

21. The composition of claim 1 wherein the compound is N-3,5-dinitrobenzoyl-N'-(2,2,2-trichloroethylidene) hydrazine.

22. The composition of claim 1 wherein the compound is present at a concentration of from 500 ppm to 1000 ppm.

* * * * *